United States Patent [19]

Rasmusson

[11] Patent Number: 5,060,640
[45] Date of Patent: Oct. 29, 1991

[54] KNEE BRACE
[75] Inventor: James K. Rasmusson, Birmingham, Mich.
[73] Assignee: Becker Orthopedic Appliance Company, Troy, Mich.
[21] Appl. No.: 493,582
[22] Filed: Mar. 14, 1990
[51] Int. Cl.⁵ .............................................. A61F 5/00
[52] U.S. Cl. ................................. 128/80 C; 128/80 F
[58] Field of Search ................... 128/75, 80 R, 80 C, 128/80 F; 623/27, 28, 39, 42, 43

[56] References Cited

U.S. PATENT DOCUMENTS

| | | | |
|---|---|---|---|
| 1,390,915 | 9/1921 | Loth | 623/39 |
| 3,528,412 | 9/1970 | McDavid | 128/80 C |
| 3,823,424 | 7/1974 | May | 623/39 |
| 3,901,223 | 8/1975 | May | 623/39 X |
| 3,902,482 | 9/1975 | Taylor | 623/39 X |
| 4,233,967 | 11/1980 | Daniell, Jr. | 129/80 C |
| 4,271,831 | 6/1981 | Deibert | 128/80 C |
| 4,573,455 | 3/1986 | Hoy . | |
| 4,599,998 | 7/1986 | Castillo | 128/77 |
| 4,697,583 | 10/1987 | Mason et al. | 128/80 C |
| 4,817,588 | 4/1989 | Bledsoe | 128/80 C |
| 4,844,057 | 7/1989 | Hoy | 128/80 C |

Primary Examiner—Robert Bahr
Assistant Examiner—Linda C. M. Dvorak
Attorney, Agent, or Firm—Jenner & Block

[57] ABSTRACT

A knee brace is provided for supporting an injured interior cruciate ligament by using straps that produce a forced couple on the knee joint to keep the tibia properly behind the femur (anti-drawering) while allowing for adjustment of the amount of anti-drawering to fit the individual needs of the patient. The knee brace may utilize a quadricentric hinge that closely approximates the natural movement of the knee joint and allows for adjustment of the knee brace to account for the natural curvature of the individual patient's leg bones. The quadricentric hinge can include four gears. Typically, these gears may be two drive gears and two idler gears.

31 Claims, 4 Drawing Sheets

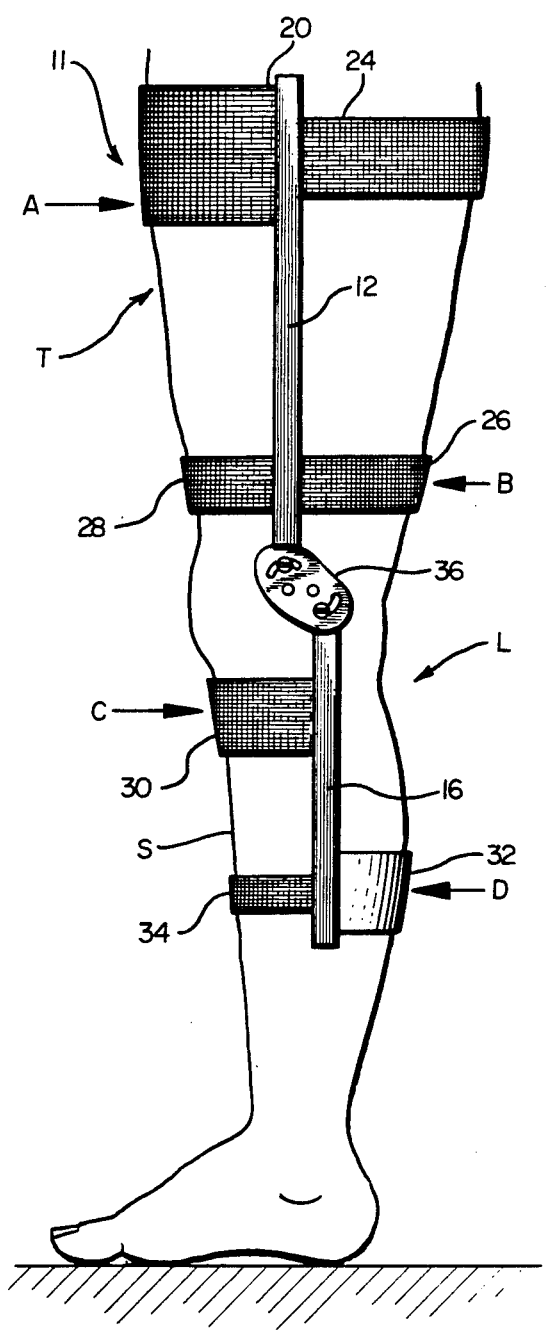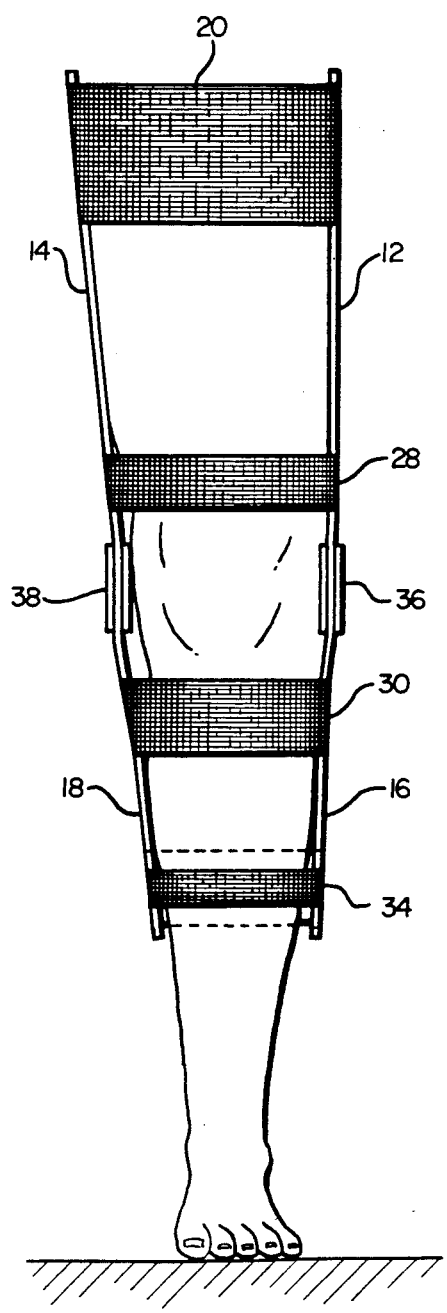

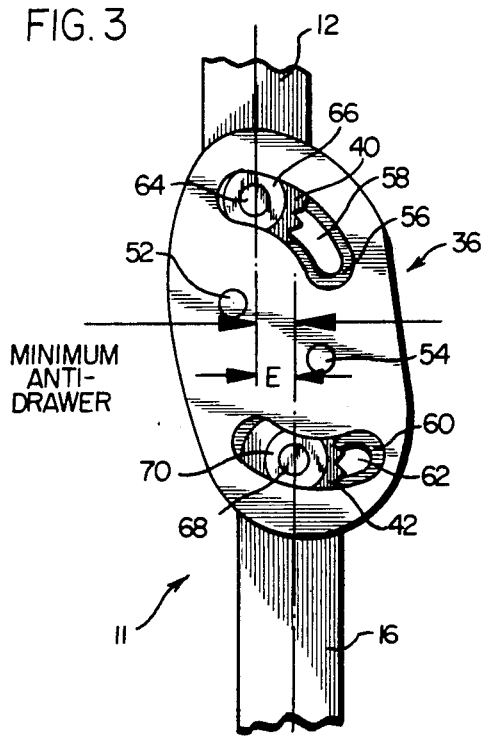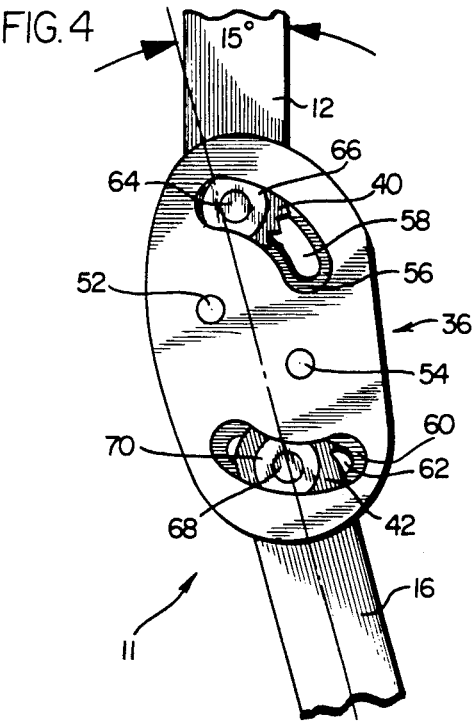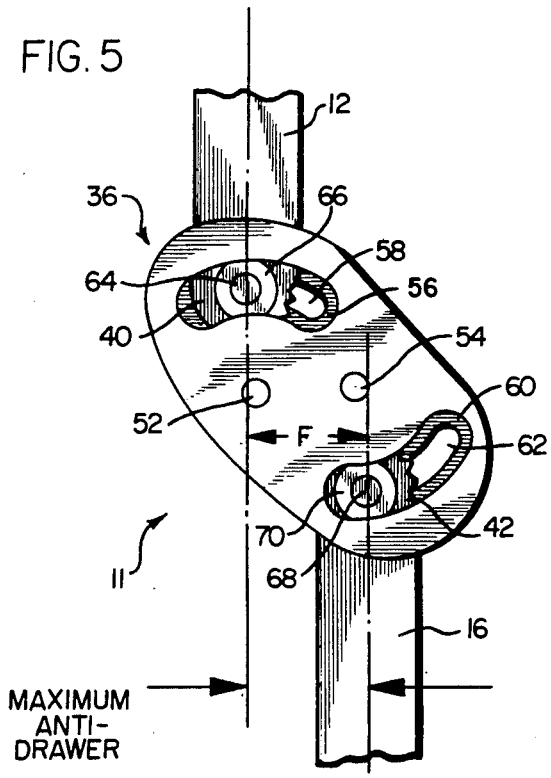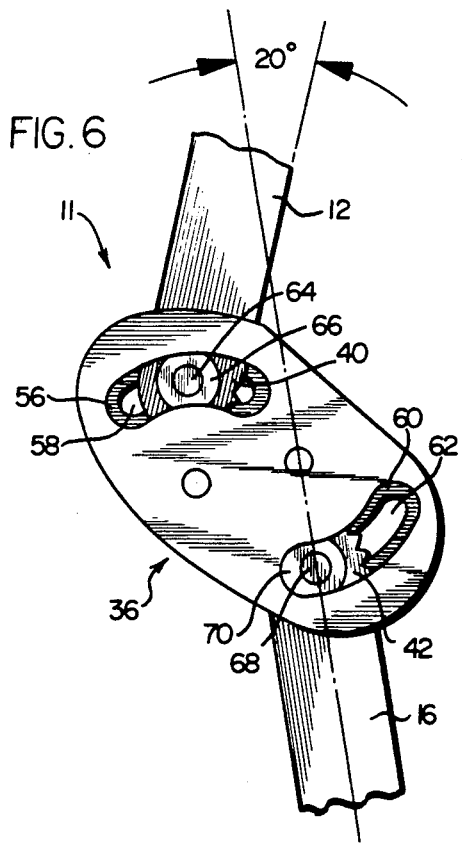

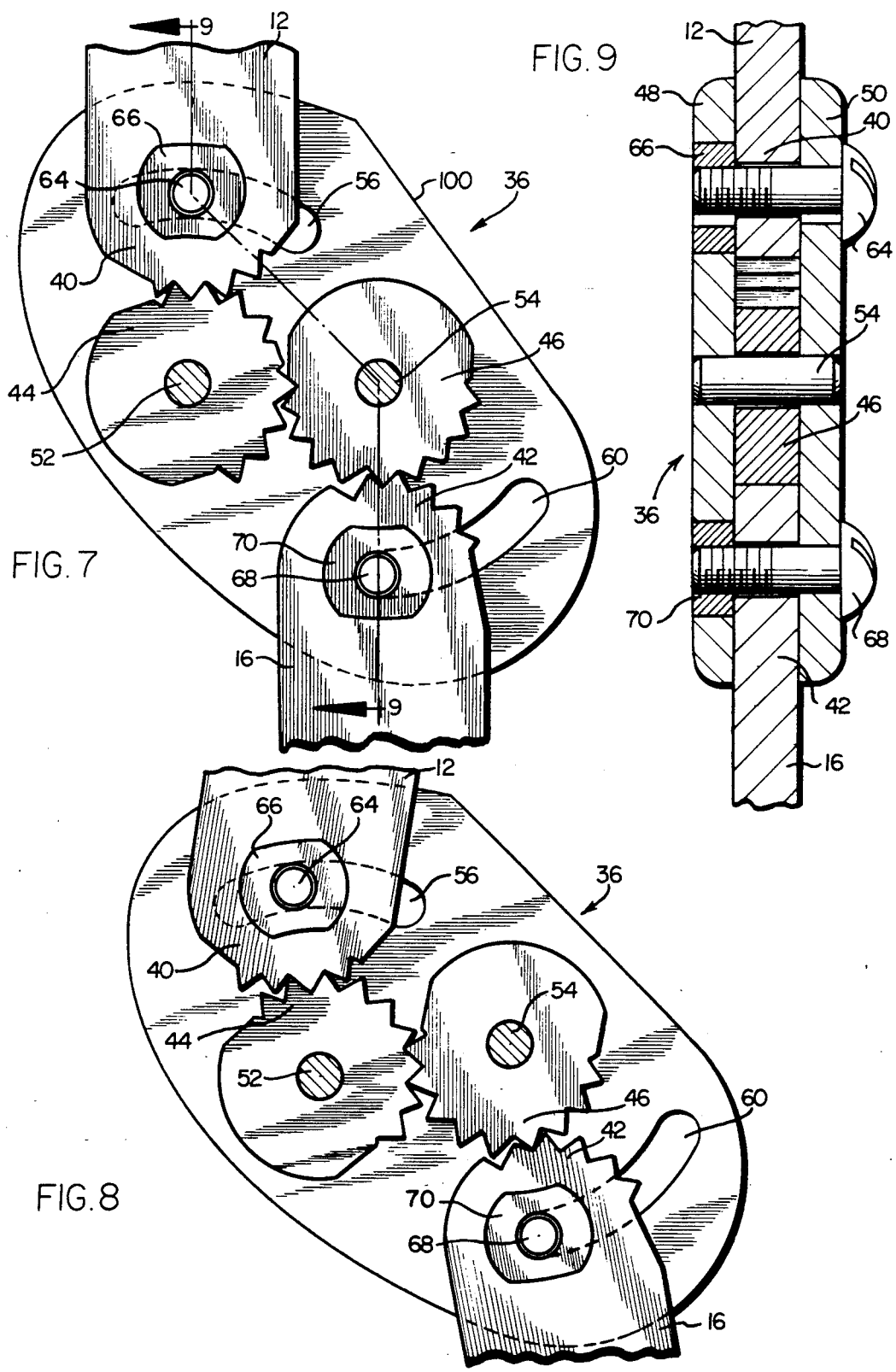

KNEE BRACE

FIELD OF THE INVENTION

This invention relates to a device for supporting an injured knee that acts as the anterior cruciate ligament.

BACKGROUND OF THE INVENTION

The human knee joint is supported by four major ligaments, including:

1. the fibular collateral ligament, arranged on the outer (lateral) side of the knee. This ligament is attached to the outer prominence of the thigh bone (the lateral femoral epicondyl) and stretches to the lateral side of the shin bone (tibia);

2. the medial collateral ligament, arranged on the inner (medial) side of the knee. This ligament is attached above to the inner prominence of the thigh bone (the medial femoral epicondyl) and below to the medial aspect of the tibia;

the central (cruciate) ligaments which cross in the center of the joint, including 3. the anterior cruciate ligament attached from the femur to the front of the tibia; and 4. the posterior cruciate ligament attached from the femur to the rear of the tibia.

The knee ligaments prevent abnormal motion of the knee and permit normal motion of the knee. All ligaments are taut when the knee is straight (extension) and are lax when the knee is bent (flexion). The anterior cruciate ligament prevents excessive forward displacement of the tibia in relation to the femur.

Excessive stress on the outside or inside of the knee joint will tear the ligaments. Athletic injuries, some of the most common knee injuries, occur when the foot is fixed on the ground while the thigh rotates inward and the leg outward, creating stress on the ligaments on the inner side of the knee. The anterior cruciate ligament may also be injured when the tibia is pushed too far forward on the thigh bone.

In most mild injuries to the knee ligaments, complete mobility may be restored if the joint is immobilized to allow the ligament time to heal. However, more severe injuries may leave permanent stiffness or lack of complete mobility, but the chance for recovery is increased if the ligament can be immobilized for a period of time.

It has been well known to use a knee brace to support an injured knee joint. Previous knee braces have been mainly concerned with providing support and preventing abnormal movement of the knee, such as over-extension, over-flexion or rotation of the joint. To accomplish this effect, previous devices have been constructed to include means on both the lateral and the medial sides of the leg to attach the brace to the leg and a hinge located at the center of the axis of rotation of the knee joint.

A known type of hinge used in prior knee braces consists of a bicentric geared hinge where there are often stops associated with the hinge gears for limiting the extent of flexion and extension.

The problems associated with these types of knee braces include the fact that they do not provide the forces necessary to act as the anterior cruciate ligament in order to prevent the tibia from moving forward of the femur. Anti-drawering is the term given to the effect of preventing the tibia from moving forward of the femur. The treating physician will often want to control the amount of anti-drawering effect of a knee brace depending on the severity of the injury and the individual characteristics of the patient's bone structure. Most of the previous devices include straps that encircle the leg to attach the brace to the leg. Some braces include rigid shells that are held onto the leg by straps. Neither of these arrangements provide the forces on the various parts of the leg necessary to keep the tibia in proper alignment.

The device disclosed in U.S. Pat. No. 4,697,583, to Mason et al. ("Mason"), purportedly provides the forces necessary to act as a substitute for the anterior cruciate ligament. The device disclosed in Mason includes strategically placed rigid and adjustable straps attached to rigid bars on either side of the leg both above and below the knee that create a force couple on the knee joint which forces the tibia backward into alignment in relation to the femur. The bars are designed to conform to the general shape of the bones, including a curved portion which is immediately adjacent to the knee. The Mason patent also discloses a bicentric hinge to provide for movement and the hinge includes stop means to control the extent of knee extension and flexion. The device disclosed in Mason does not, however, allow for any adjustment of the anti-drawering effect and therefore, no adjustment of the relative position of the tibia and the femur. Because of its arrangement, with the attachment bars having a set curvature to account for the natural position of the bones, the device disclosed in Mason cannot be adjusted to fit the particular anti-drawering needs of an individual patient, especially with respect to the patient's changing anti-drawering needs as the postsurgical healing process progresses.

The straps of Mason which attach the brace to the leg only encompass a portion of the leg and therefore, the rigid straps must be individually formed to fit an individual's particular leg size or the straps must be made in general leg sizes which may cause discomfort to the patient.

SUMMARY OF THE INVENTION

The present invention overcomes the problems of prior devices by providing a knee brace with a quadricentric hinge that allows the orthopedist to adjust the amount of anti-drawering effect to fit the individual needs of each patient.

In accordance with one aspect of the present invention, a knee brace is provided for supporting an injured anterior cruciate ligament by using straps that produce a force couple on the knee joint to keep the tibia properly behind the femur (anti-drawering), while allowing for adjustment of the amount of anti-drawering to fit the individual needs of the patient.

In accordance with another aspect of the present invention, a knee brace is provided for supporting an injured anterior cruciate ligament with a quadricentric hinge that closely approximates the natural movement of the knee joint and allows for adjustment of the brace to account for the natural curvature of the individual patient's leg bones.

In accordance with yet another aspect of the present invention, a knee brace is provided for supporting an injured anterior cruciate ligament that may be mass produced and yet may be adjusted to fit the needs of individual patients.

The knee brace of the present invention includes at least two bars to be attached above the knee joint and at least two bars attached below the knee joint. These bars not only stabilize the knee joint, but also prevent any unnatural rotational movement of the knee. These bars are attached to the patient's leg at four points. The first point is at the top of the thigh where an anterior thigh cuff is attached. The anterior thigh cuff provides a force backward on the front of the upper thigh.

The second point of contact is at the lower thigh just above the knee joint. There, a distal posterior thigh strap applies a force forward on the back of the leg.

The lower bars are attached to the leg by an adjustable tibia strap just below the knee joint. The tibia strap applies a force backward on the front of the shin.

The final strap is a rigid distal shin cuff which applies a forwardly directed force to the back of the lower calf.

The upper and lower rigid bars are joined by a quadricentric hinge. A quadricentric hinge is one which contains four axes of pivotable rotation. The quadricentric hinge is adjustable to allow for adjustment of the tibia in relation to the femur.

The quadricentric hinge can comprise four gears, two drive gears and two idler gears. The drive gears are attached to the ends of the rigid bars and have structure sufficient to allow for adjustment of the amount of anti-drawering effect and the amount of extension and flexion of the knee. The idler gears, on the other hand, have fixed pivot points and intermesh at the anatomical center of the knee.

The quadricentric hinge allows the position of the drive gears to be adjusted to account for the natural curvature of the leg bones for each individual patient without changing any parts on the brace. This overcomes the problems in the previous devices where doctors were required to either change the rigid bars to fit the individual patient or use rigid bars that only approximated the individual's natural bone structure. Now, one device may be used on a wide variety of patients, thus reducing cost and facilitating mass production.

BRIEF DESCRIPTION OF THE DRAWINGS

FIG. 1 is a side view of the knee brace;

FIG. 2 is a front view of the knee brace;

FIG. 3 is a plan view of the quadricentric hinge joint showing the hinge set at the minimum anti-drawer setting;

FIG. 4 is a plan view of the quadricentric hinge joint showing the hinge set at the minimum anti-drawer and also set for a 15° extension stop;

FIG. 5 is a plan view of the quadricentric hinge joint showing the hinge set at the maximum anti-drawer setting;

FIG. 6 is a plan view of the quadricentric hinge joint showing the hinge set at the maximum anti-drawer and also set for a 20° extension stop;

FIG. 7 is a plan view of the quadricentric hinge joint;

FIG. 8 is a plan view of the quadricentric hinge joint showing the engagement of the gears as the knee joint moves;

FIG. 9 is a cross-sectional view of the quadricentric hinge joint; and

DETAILED DESCRIPTION OF THE PREFERRED EMBODIMENT

Figure 10:
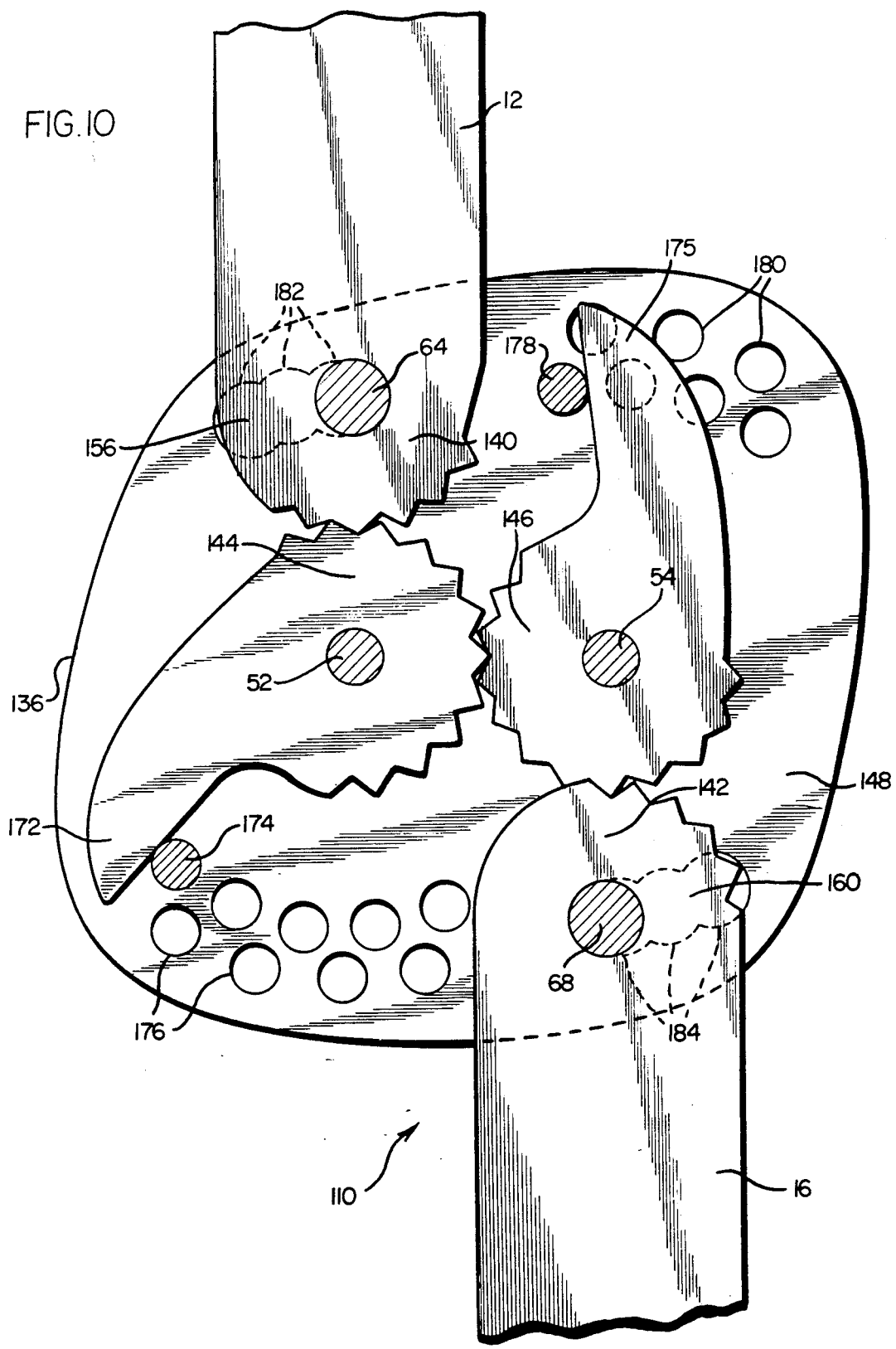
FIG. 10 is a plan view of the quadricentric hinge joint showing spur idler gears with flexion and extension stops.

Referring to the Figures generally and in particular to FIG. 1, a novel knee brace 11 is illustrated which supports an injured knee joint, specifically providing support for an injured anterior cruciate ligament by providing a force couple on the person's leg L. More specifically, brace 11 is designed to produce a first force A on the upper front portion of a person's thigh T, a second force B on the lower rear portion of the person's thigh T, a third force C on the upper front portion of the person's shin S, and a fourth force D on the lower rear portion of the person's shin S. Together with the quadricentric hinge joint 36, these forces allow the treating physician to adjust the alignment of the person's tibia relative to his or her femur.

Now referring to FIG. 1 and FIG. 2 in combination, knee brace 11 may comprise a lateral femoral bar 12, a medial femoral bar 14, a lateral tibia bar 16 and a medial tibia bar 18. The femoral bars are connected by a rigid proximal anterior thigh cuff 20 which extends across the front of the person's leg L. Anterior thigh cuff 20 is held firmly in place against the person's leg L by use of an adjustable proximal posterior thigh strap 24, which may be adjusted to insure that the curvature of anterior thigh cuff 20 corresponds to the curvature of the person's thigh T. The adjustment may be accomplished through known means such as a buckle. Proximal posterior thigh strap 24 may also be used to adjust the amount of force A that anterior thigh cuff 20 exerts on the front of the person's thigh T.

Femoral bars 12 and 14 are also connected by a reinforced adjustable distal posterior thigh strap 26. Distal posterior thigh strap 26 exerts a force B on the back of the person's thigh T. Distal posterior thigh strap 26 is held firmly in place against the person's leg by use of a reinforced anterior thigh strap 28, which may be adjusted to insure that the curvature of distal posterior thigh strap 26 corresponds to the curvature of the person's leg. Anterior thigh strap 28 may also be used to adjust the strength of force B which distal posterior thigh strap 26 exerts on the back of the person's leg.

Lateral tibia bar 16 and medial tibia bar 18 are connected by an adjustable proximal tibia strap 30. Proximal tibia strap 30 exerts a force C on the front of the person's shin S.

Tibia bars 16 and 18 are also connected by a rigid distal tibia cuff 32, which exerts a force D on the back portion of the person's calf G. The curvature of distal tibia cuff 32 is adjustable by use of an adjustable distal anterior shin strap 34. Distal anterior shin strap 34 may also be used to adjust the strength of force D exerted on the back of the person's leg L.

Lateral femoral bar 12 and lateral tibia bar 16 are joined at the knee joint by a quadricentric hinge joint 36. Likewise, medial femoral bar 14 and medial tibia bar 18 are joined at the knee joint by a quadricentric hinge joint 38 similar to quadricentric hinge joint 36.

Referring to FIGS. 7-9, quadricentric hinge joint 36 comprises a femoral drive gear 40, a tibia drive gear 42, an anterior idler gear 44, a posterior idler gear 46, an outer cover 48 and an inner cover 50. Femoral drive gear 40 is an extension of femoral bar 12. Likewise, tibia drive gear 42 is an extension of tibia bar 16. Femoral drive gear 40 intermeshes with anterior idler gear 44. Similarly, tibia drive gear 42 intermeshes with posterior idler gear 46. Knee brace 11 is preferably designed so that idler gears 44 and 46 intermesh at the anatomical center of the knee joint. The gear teeth on the gears do not extend around the entire circumference of the gears, thus creating limits of flexion and extension at the ends of the gear teeth, as is shown in FIG. 8.

Anterior idler gear 44 is fixed about an axis of rotation by a pin 52. Likewise, posterior idler gear 46 is fixed about an axis of rotation by a pin 54. On the other hand, femoral drive gear 40 has an axis of rotation which is movable along a generally arcuate path circumscribed by a groove 56 in outer cover 48 and a groove 58 in inner cover 50. In a similar fashion, tibia drive gear 42 has an axis of rotation which is movable along a generally arcuate path circumscribed by a groove 60 in outer cover 48 and a groove 62 in inner cover 50. The axis of rotation of femoral drive gear 40 may be moved and fixed at any point along the generally arcuate path by loosening and tightening a screw 64 and a complementary nut 66. The axis of rotation of tibia drive gear 42 may also be moved and fixed at any point along the generally arcuate path by loosening and tightening a screw 68 and a complementary nut 70.

Referring to FIGS. 3-6, in operation the amount of anti-drawering effect desired may be adjusted to fit the individual patient's needs. Specifically referring to FIG. 3, knee brace 11 may be adjusted to allow for a minimum amount of anti-drawering. By adjusting the position of screws 64 and 68 in grooves 56 and 60, respectively, knee brace 11 may be affixed in a position where the distance "E," the offset, between the relative position of tibia bar 16 and femoral bar 12, is at a minimum.

FIG. 5 shows knee brace 11 adjusted to a position wherein the distance "F," the offset, between the relative position of the tibia bar 16 and the femoral bar 12, is at a maximum. This position provides the maximum amount of anti-drawering effect.

FIG. 4 shows knee brace 11 where screw 68 has been adjusted in grooves 60 and 62 to allow for a 15° extension stop of leg L. Likewise, as shown in FIG. 6, screw 64 may be adjusted in grooves 56 and 58 to allow for a certain amount of extension stop, here about 20°.

FIG. 10 shows an alternative construction of a brace 110 and a quadricentric hinge joint 136, wherein an anterior idler gear 144 includes a flexion adjustment spur 172. Likewise, a posterior idler gear 146 includes an extension adjustment spur 175. Flexion adjustment spur 172 engages a flexion adjustment pin 174 which extends through one of a plurality of flexion adjustment apertures 176 in outer cover 148. Flexion adjustment apertures 176 are preferably spaced to allow for adjustment of the amount of allowable flexion at regular intervals, such as about 15° intervals. Similarly, extension adjustment spur 175 engages an extension adjustment pin 178 which extends through one of a plurality of extension adjustment apertures 180 in outer cover 148 and a complementary aperture in the corresponding inner cover (not shown). Again, extension adjustment apertures 180 are spaced to allow for adjustment of the allowable extension at regular intervals.

Also shown in FIG. 10, outer femoral drive gear adjustment groove 156, inner femoral drive gear adjustment groove (not shown), outer tibia drive gear adjustment groove 160, and inner tibia drive gear adjustment groove (not shown), may be constructed to comprise finite positions for screws 64 and 68. In this way, the axes of rotation of femoral drive gear 140 and tibia drive gear 142 may be fixed at predetermined finite positions along a generally arcuate path to provide for adjustment of the amount of anti-drawering effect provided by the knee brace 110.

Preferably, both outer drive gear adjustment grooves 156 and 160 include a plurality of indents 182 and 184. These indents can fix the axes of drive gears 140 and 142 in specified positions defined by indents 182 and 184. Additionally, the defined indents allow a specified anti-drawer setting to be readily achieved. Similar indents may be provided in both inner drive gear adjustment grooves (not shown).

When the brace 110 or 11 is affixed to a person's leg, the circumference of the various straps will be adjusted to fit the circumference of the person's leg. For example, brace 11 is affixed by adjusting proximal posterior thigh strap 24, distal anterior thigh strap 28, and distal anterior shin strap 34. This will also adjust the amount of forces A, B, C, and D exerted on the person's leg L. The amount of anti-drawering effect provided by quadricentric hinges 36 and 38 will then be adjusted. By doing this, injury or aggravation of injury to the anterior cruciate ligament can be prevented by forcing the tibia to remain in a position posterior to the femur. In order to adjust the amount of anti-drawering effect, screw 64 is loosened and positioned along grooves 56 and 58, and then screw 68 is loosened and positioned along grooves 60 and 62. Screws 64 and 68 can be positioned to provide an anti-drawering effect so that the tibia is positioned anywhere from a minimum distance "E" behind the femur, to a maximum distance "F" behind the femur.

The amount that the knee joint may be flexed can then be adjusted by positioning flexion adjustment pin 174 in the desired flexion adjustment aperture 176 to provide a predetermined amount of flexion stop. The amount that the knee joint may be extended can be adjusted by positioning the extension adjustment pin 178 in the extension adjustment apertures 180 to provide a predetermined amount of extension.

I claim:

1. An adjustable knee brace for supporting a person's injured anterior cruciate ligament by applying a force couple to the femur and the tibia, comprising:

a medial femoral bar and a lateral femoral bar;

first attachment means connected to the upper portion of the medial femoral bar and the upper portion of the lateral femoral bar for attaching the leg brace to a person's leg and for applying a posteriorly directed force against the front of the thigh distally of the knee joint;

second attachment means connected to the lower portion of the medial femoral bar and the lower portion of the lateral femoral bar for attaching the leg brace to a person's leg and for applying an anteriorly directed force against the back of the leg proximal the knee joint;

a medial tibia bar and a lateral tibia bar;

third attachment means connected to the upper portion of the medial tibia bar and the upper portion of the lateral tibia bar for attaching the knee brace to a person's leg and for applying a posteriorly directed force against the front of the shin proximal the knee joint;

fourth attachment means connected to the lower portion of the medial tibia bar and the lower portion of the lateral tibia bar for attaching the knee brace to a person's leg and for applying an anteriorly directed force against the back of the shin distally of the knee joint;

a first quadricentric hinge joining the medial femoral bar and the medial tibia bar and a second quadricentric hinge joining the lateral femoral bar and the lateral tibia bar, each said quadricentric hinge including four serial intermeshing pivotable gear members having parallel axes of pivotable rotation; and said quadricentric hinges having adjustment means for adjusting the position of the tibia bars relative to the femoral bars, to permit positioning of the tibia with relation to the femur to achieve an anti-drawering effect.

2. The adjustable knee brace of claim 1, wherein the first attachment means comprises a proximal anterior thigh cuff extending across the front of the thigh from the medial femoral bar to the lateral femoral bar distally of the knee joint.

3. The adjustable knee brace of claim 2, wherein the proximal anterior thigh cuff is substantially rigid.

4. The adjustable knee brace of claim 1, wherein the second attachment means comprises a distal posterior thigh strap extending across the back of the thigh from the medial femoral bar to the lateral femoral bar proximal the knee joint.

5. The adjustable knee brace of claim 4, wherein the distal posterior thigh strap is substantially rigid.

6. The adjustable knee brace of claim 4, wherein the proximal posterior thigh strap includes a reinforced adjustable anterior thigh strap.

7. The adjustable knee brace of claim 1, wherein the third attachment means comprises a proximal tibia strap extending across the front of the shin from the medial tibia bar to the lateral tibia bar proximal the knee joint.

8. The adjustable knee brace of claim 7, wherein the proximal tibia strap is substantially rigid.

9. The adjustable knee brace of claim 1, wherein the fourth attachment means comprises a distal posterior tibia cuff extending across the back of the shin from the medial tibia bar to the lateral tibia bar.

10. The adjustable knee brace of claim 9, wherein the distal posterior tibia cuff is substantially rigid.

11. The adjustable knee brace of claim 1, wherein the medial femoral bar is substantially straight.

12. The adjustable knee brace of claim 1, wherein the lateral femoral bar is substantially straight.

13. The adjustable knee brace of claim 1, wherein the medial tibia bar is substantially straight.

14. The adjustable knee brace of claim 1, wherein the lateral tibia bar is substantially straight.

15. An adjustable knee brace for supporting a person's injured anterior cruciate ligament by applying a force couple to the femur and the tibia, comprising:
a medial femoral bar and a medial tibia bar, a lateral femoral bar and a lateral tibia bar;
attachment means for attaching the brace to the person's leg and for connecting the medial femoral bar to the lateral femoral bar and for connecting the medial tibia bar to the lateral tibia bar and for applying a force couple to the femur and the tibia to force the tibia backward in relation to the femur;
a pair of quadricentric hinges, one of said hinges located on the medial side of the leg and the other of said hinges located on the lateral side of the leg,
each quadricentric hinge having four serially intermeshing gears with parallel axes of pivotable rotation, said four gears including a first drive gear attached to the lower end of the femoral bar, which intermeshes with a first idler gear, a second drive gear attached to the upper end of the tibia bar, which intermeshes with a second idler gear, the first idler gear and the second idler gear capable of intermeshing about an axis adjacent to the anatomical center of the knee joint.

16. The adjustable knee brace of claim 15, wherein the adjustable means for adjusting the axes of rotation for the first drive gear and the second drive gear comprises at least one aperture following a generally arcuate path located in the outer cover and at least one aperture following a generally arcuate path located in the inner cover, adjustable screw means through the center of the first drive gear and the second drive gear, said screw means extending into said apertures in the outer and inner covers; said apertures being positioned to control the relative movement of the first drive gear and the second drive gear.

17. The adjustable knee brace of claim 16, wherein the adjustable crew means includes a screw with its head on the outside of the aperture located in the outer cover and which extends though the center of the drive gear and out of the aperture located in the inner cover, a nut which is attached to the end of said screw adjacent to the inner cover, whereby the screw may be loosened to position the screw in the aperture and tightened, thus adjusting the relative position of the first drive gear and the second drive gear.

18. The adjustable knee brace of claim 17, wherein the amount of extension and flexion of the knee joint is controlled by the location of the screws in the apertures.

19. An adjustable knee brace for supporting a person's anterior cruciate ligament by applying a force couple to the femur and the tibia, comprising:
femoral attachment means for attaching the leg brace to the upper portion of the person's leg;
said femoral attachment means including a medial femoral element and a lateral femoral element, a first force producing means positioned at the upper portion of the medial and lateral femoral elements for producing a posteriorly directed force against the front of the person's thigh, a second force producing means positioned at the lower portion of the medial and lateral femoral elements for producing an anteriorly directed force against the back of the person's thigh;
tibia attachment means for attaching the leg brace to the lower portion of the person's leg;
said tibia attachment means including a medial tibia element and a lateral tibia element, a third force producing means positioned at the upper portion of the medial and lateral tibia elements for producing a posteriorly directed force against the front of the person's shin, a fourth force producing means positioned at the lower portion of the medial and lateral tibia elements for producing an anteriorly directed force against the back of the person's shin;
hinge means for connecting the tibia attachment means to the femoral attachment means;
said hinge means including a first axis of rotation located at the lower end of the femoral attachment, a second axis of rotation located at the upper end of the tibia attachment means, a third axis of rotation adjacent to the first axis of rotation, a fourth axis of rotation adjacent to the second axis of rotation;
said third axis of rotation and said fourth axis of rotation being equidistant from the anatomical center of the knee joint, said first axis of rotation and said second axis of rotation including adjustment means for positioning the medial and lateral tibia elements relative to the medial and lateral femoral elements, to align the person's tibia behind the femur to facilitate healing of the injured anterior cruciate ligament.

20. A hinge for joining an upper portion and a lower portion of a knee brace, said hinge comprising:
a first drive means for pivoting about a first movable axis, said first drive means interfacing with a first idler means for pivoting about a first fixed axis;
a second drive means for pivoting about a second movable axis, said second drive means interfacing with a second idler means for pivoting about a second fixed axis;
said first idler means and said second idler means interfacing at the anatomical center of the knee;
said first movable axis including first adjustment means for allowing the first movable axis to be moved along a first generally arcuate path and to be temporarily fixed at any position along the first generally arcuate path;
said second movable axis including second adjustment means for allowing the second movable axis to be moved along a second generally arcuate path and to be temporarily fixed at any position along the second generally arcuate path.

21. The hinge of claim 20, wherein the first drive means comprises a first drive gear.

22. The hinge of claim 21, wherein the second drive means comprises a second drive gear.

23. The hinge of claim 22, wherein the first idler means comprises a first idler gear.

24. The hinge of claim 23, wherein the second idler means comprises a second idler gear.

25. The hinge of claim 24, wherein the first adjustment means comprises:
an outer cover and a inner cover overlaying at least a portion of each of the first drive gear, the second drive gear, the first idler gear and the second idler gear;
at least one aperture following a first generally arcuate path located in both the outer cover and the inner cover;
first adjustable positioning means for positioning the first movable axis, said adjustable positioning means extending through the apertures in the outer cover and the inner cover along the first generally arcuate path;
the first movable axis being positionable and fixable along the first generally arcuate path.

26. The hinge of claim 25, wherein the second adjustment means comprises:
an outer cover and a inner cover overlaying at least a portion of each of the first drive gear, the second drive gear, the first idler gear and the second idler gear;
at least one aperture following a second generally arcuate path located in both the outer cover and the inner cover;
second adjustable positioning means for positioning the second movable axis, said adjustable positioning means extending through the aperture in the outer cover and the inner cover;
the second movable axis being positionable and fixable along the second generally arcuate path.

27. The hinge of claim 26, wherein the first idler gear includes flexion adjustment means for adjusting the amount of flexion of the knee joint.

28. The hinge of claim 27, wherein the flexion adjustment means comprises:
a first spur located on said first idler gear;
a plurality of apertures located in the outer cover which follow a generally arcuate path and a plurality of apertures located in the inner cover following a corresponding generally arcuate path;
stop means insertable in the apertures in the outer cover which extends to the apertures in the inner cover for contacting said first spur located on said first idler gear to control the extent of extension and flexion of the knee joint.

29. The hinge of claim 26, wherein the second idler gear includes extension adjustment means for adjusting the amount of extension of the knee joint.

30. The hinge of claim 29, wherein the extension adjustment means comprises:
a second spur located on said second idler gear;
a plurality of apertures located in the outer cover which follow a generally arcuate path and a plurality of apertures located in the inner cover following a corresponding generally arcuate path;
second stop means insertable in the apertures in the outer cover which extends to the apertures in the inner cover for contacting said second spur located on said second idler gear to control the extent of extension of the knee joint.

31. The adjustable knee brace of claim 15, wherein each quadricentric hinge further comprises an outer cover and an inner cover overlaying at least a portion of said drive gears and said idler gears, pin means through the center of the first idler gear and the second idler gear attaching the outer cover to the inner cover while allowing the idler gears to pivot about an axis, adjustable means for adjusting the axes of rotation for the first drive gear and the second drive gear to adjust and fix the position of the rigid tibia bar relative to the position of the rigid femur bar to provide a preselected amount of anti-drawering.

* * * * *

UNITED STATES PATENT AND TRADEMARK OFFICE
CERTIFICATE OF CORRECTION

PATENT NO. : 5,060,640

DATED : October 29, 1991

INVENTOR(S) : James K. Rasmusson

It is certified that error appears in the above-identified patent and that said Letters Patent is hereby corrected as shown below:

Col. 7, line 23, delete "proximal" and insert therefor --distal--.

Col. 8, line 14, delete "crew" and insert therefor --screw--; and line 16, delete "though" and insert therefor --through--.

Col. 9, line 2, delete "the" and insert therefor --an--.

Signed and Sealed this

Ninth Day of March, 1993

Attest:

STEPHEN G. KUNIN

Attesting Officer

Acting Commissioner of Patents and Trademarks